(12) United States Patent
Riggs et al.

(10) Patent No.: US 10,390,476 B2
(45) Date of Patent: Aug. 27, 2019

(54) FUNGICIDAL COMPOSITIONS AND METHODS

(75) Inventors: Jennifer Riggs, Raleigh, NC (US); David Doran, Lebanon, IN (US)

(73) Assignee: Bayer CropScience LP, Research Triangle Park, NC (US)

( * ) Notice: Subject to any disclaimer, the term of this patent is extended or adjusted under 35 U.S.C. 154(b) by 416 days.

(21) Appl. No.: 13/885,269

(22) PCT Filed: Nov. 23, 2011

(86) PCT No.: PCT/US2011/062053
§ 371 (c)(1),
(2), (4) Date: Aug. 22, 2013

(87) PCT Pub. No.: WO2012/071520
PCT Pub. Date: May 31, 2012

(65) Prior Publication Data
US 2013/0324400 A1    Dec. 5, 2013

Related U.S. Application Data

(60) Provisional application No. 61/415,958, filed on Nov. 22, 2010.

(51) Int. Cl.
*A01N 37/50*   (2006.01)
*A01N 43/40*   (2006.01)
(Continued)

(52) U.S. Cl.
CPC .............. *A01C 1/06* (2013.01); *A01N 37/50* (2013.01); *A01N 43/40* (2013.01); *A01N 51/00* (2013.01); *A01N 63/02* (2013.01)

(58) Field of Classification Search
CPC ....................................................... A01N 43/40
See application file for complete search history.

(56) References Cited

U.S. PATENT DOCUMENTS 7,572,818 B2 *   8/2009   Mansfield et al. ............. 514/357
8,648,101 B2 *   2/2014   Suwa ............................. 514/357
(Continued)

FOREIGN PATENT DOCUMENTS

CN          1674784 A        9/2005
DE    102009001732 A1 *      9/2010    ............. A01N 37/50
(Continued)

OTHER PUBLICATIONS

International Search Report of PCT/US62053 dated Jun. 14, 2012.
(Continued)

*Primary Examiner* — Alton N Pryor

(57) ABSTRACT

Provided are methods for reducing the occurrence of sudden death syndrome in plants, such as soybeans, using compounds of the general formula (I).

9 Claims, 6 Drawing Sheets

(51) Int. Cl.
*A01N 51/00* (2006.01)
*A01N 63/02* (2006.01)
*A01C 1/06* (2006.01)

(56) References Cited

U.S. PATENT DOCUMENTS

| | | | |
|---|---|---|---|
| 2005/0234110 A1 | 10/2005 | Mansfield et al. | |
| 2007/0123541 A1 | 5/2007 | Grosjean-Cournoyer | |
| 2007/0173408 A1 | 7/2007 | Tormo I Blasco | |
| 2007/0191398 A1 | 8/2007 | Tormo I Blasco | |
| 2010/0048647 A1 | 2/2010 | Suwa | |
| 2010/0107281 A1* | 4/2010 | Cochran | A01N 43/82 800/298 |
| 2010/0130357 A1* | 5/2010 | Hungenberg et al. | 504/100 |
| 2010/0249193 A1 | 9/2010 | Andersch | |
| 2014/0056866 A1* | 2/2014 | Andersch | A01N 43/40 424/93.461 |

FOREIGN PATENT DOCUMENTS

| | | | |
|---|---|---|---|
| EP | 2036438 A1 | 3/2009 | |
| EP | 2039772 A2 * | 3/2009 | A01N 43/40 |
| WO | 2004016088 A2 | 2/2004 | |
| WO | 2005077179 A1 | 8/2005 | |
| WO | 2005077183 A1 | 8/2005 | |
| WO | 2005087773 A1 | 9/2005 | |
| WO | 2005112643 A1 | 12/2005 | |
| WO | 2007101804 A1 | 9/2007 | |
| WO | 2008126922 A1 | 10/2008 | |
| WO | 2010012964 A2 | 9/2010 | |
| WO | 2010108616 A1 | 9/2010 | |

OTHER PUBLICATIONS

K.S. McLean et al., "In vitro suppression of Fusarium solani, the causal agent of sudden death syndrome of soybean", Phytopathology, vol. 84, No. 10 (Oct. 1, 1994), p. 1115.

K.S. McLean et al., "Fungicide suppression of Fusarium solani, the causal agent of suddent death syndrome of soybean", Journal of Nematology, vo. 27, No. 4 (Dec. 1, 1995), p. 509.

Andreas Westphal et al., "Sudden death syndrome", The Plant Health Instructor, Jan. 1, 2008, pp. 1-8, https://www.apsnet.org/edcenter/intropp/lessons/fungi/ascomycetes/Pages/SuddenDeath.aspx.

"Diseases of Soybean—Sudden Death Syndrome", Purdue Extension Knowledge to Go, Apr. 1, 2006, pp. 1-4, http://www.extension.purdue.edu/extmedia/BP/BP-58-W.pdf.

Takayuki Aoki et al., "Sudden-death syndrome of soybean is caused by two morphologically and phylogenetically distinct species within the Fusarium solani species complex—F. virguliforme in North American and F. tucumaniae in South America", Mycologia (Apr. 1,2003), pp. 660-684.

J.D. Weems et al., "Effect of Fungicide Seed Treatments on Fusarium virguliforme and Sudden Death Syndrome of Soybean", American Pathological Society North Central Division Annual Meeting (Jun. 8, 2010), p. 1; also available as thesis with University of Illinois (Jul. 1, 2011), pp. 1-72.

Brent James Pacha, "Soybean seedling emergence and yield in the presence of Fusarium virguliforme", Thesis, Iowa State University (Jan. 1, 2010), http://lib.dr.iastate.edu/etd/11560.

Westphal, et al., "Diseases of Soybean. Sudden Death Syndrome," May 1, 2006. [Retrieved from the Internet Mar. 8, 2012: <http://www.ces.purdue.edu/extmedia/BP/BP-58-W.pdf>] p. 2, col. 1.

Extended European Search Report, European Patent Application No. 11843865.4, dated Mar. 27, 2014, 18 pages.

Xing, L, et al., "Effects of Crop Rotation of Soybean with Corn on Severity of Sudden Death Syndrome and Population Densities of Heterodera Glycines in Naturally Infested Soil," Field Crop Research, 2009, vol. 112, pp. 107-117.

* cited by examiner

FUNGICIDAL COMPOSITIONS AND METHODS

BACKGROUND

1. Field

The present invention relates to methods and compositions for preventing, treating, and/or ameliorating fungal diseases and/or nematodes in plants via application to plant roots, seed, and/or soil of at least one pyridinyl ethylbenzamide derivative.

2. Description of Related Art

Sudden death syndrome (SDS) of soybean (*Glycine max*) is one of the most economically devastating plant diseases in the United States. It is among the top yield-destroying soybean diseases, with average losses exceeding $190 million per year. Yield losses are commonly between 20% and 50%, and yield losses of 100% have been reported in heavily-infested areas.

First discovered in Arkansas in 1971, SDS has been reported throughout most of the north central United States, including Illinois, Indiana, Iowa, Kansas, Kentucky, Minnesota, Mississippi, Missouri, Nebraska, Ohio, and Tennessee. SDS has also been reported in Canada, Argentina, and Brazil, for example. The disease appears to be most severe when soybeans are planted early into cool, wet soils and when heavy mid-summer rains saturate the soil.

In North America, SDS is reportedly caused by the soilborne fungus *Fusarium solani* f. sp. *glycines*, also known as *Fusarium virguliforme*, while in South America SDS appears to be caused by *Fusarium tucumaniae*. Although the pathogen colonizes soybean roots, causing root rot and vascular discoloration of roots and stems, the most evident early symptoms of SDS include mottling and mosaic of the leaves. Later, intraveinal chlorosis and/or necrosis (yellow and/or brown spots, respectively, on leaves) develops, followed by sudden leaf drop with retention of petioles (leaf stalks). The pathogen has been isolated from soybean roots and lower stems, but not leaves. The foliar symptoms are believed to be caused by fungal toxins produced on or within infected roots, which are then transported to the leaves.

Current SDS management options are limited. Although soybean varieties less sensitive to SDS have been developed, there are no highly resistant varieties; soybean breeders are developing SDS-resistant varieties, but progress has been slow. To date, fungicides applied in furrow during planting or as seed treatments have shown only limited effects. Attempts to apply fungicides to foliage have no effect on SDS, presumably because the fungal infection is restricted to root systems and fungicides typically do not move downward in the plant to reach the site of infection.

When symptoms first appear in a field, they may be localized to a few small areas—often those that are wet or compacted, such as turn rows. Symptomatic areas may expand over the subsequent weeks, and non-adjacent areas in the field may also exhibit symptoms. Because the *Fusarium* fungus can overwinter in soil, areas of a field that show symptoms of the disease often grow larger with each growing season.

Also, corn (maize) may be a host for the *Fusarium* pathogen, as it reportedly survives on corn kernels and other corn debris. Severe SDS has been reported in corn/soybean rotation fields where no SDS was observed previously. Presumably, *Fusarium* survives the winter as chlamydospores in the crop residue or freely in the soil. Chlamydospores can withstand wide soil temperature fluctuations (including freezing) and resist desiccation. As soil temperatures rise in the spring, chlamydospores near soybean roots are stimulated to germinate, then infect soybean roots.

There appear to be several factors that influence the spread and the severity of SDS. One of those factors is soybean cyst nematode (SCN). *Fusarium virguliforme* has been found inside SCN cysts, leading to speculation that these two agents both contribute to SDS symptoms. While SDS has been observed in the absence of SCN, damage due to SDS is much greater in susceptible soybean varieties when both pathogens are present than when either pathogen is present alone.

Without wishing to be bound by theory, other factors that contribute to SDS may include: susceptibility of particular soybean varieties; cool, damp conditions; early planting time; seed quality; soil compaction; and genetic diversity within the *Fusarium virguliforme* genome itself.

Despite wide recognition of this problem, available treatments have little to no impact on SDS; the solution is provided by the embodiments characterized in the claims.

BRIEF SUMMARY

In one embodiment, a method for reducing the occurrence of sudden death syndrome is provided, comprising applying an effective amount of a composition comprising a compound of general formula (I):

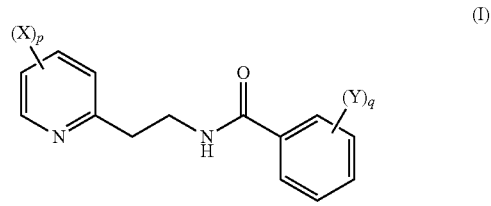

(I)

or a salt or N-oxide thereof to a plant seed, to soil in which a plant is growing or in which it is desired to grow it, to plant roots, or to combinations thereof;

wherein:
  p is an integer equal to 1, 2, 3 or 4;
  q is an integer equal to 1, 2, 3, 4 or 5;
  each X is independently selected from the group consisting of halogen, alkyl, and haloalkyl, provided that at least one X is a haloalkyl;
  each Y is independently selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

In one aspect, p is 2. In one aspect, q is 1 or 2, and the substituent(s) Y is/are positioned in the ortho position of the benzene ring. In one aspect, the compound corresponds to general formula (I'):

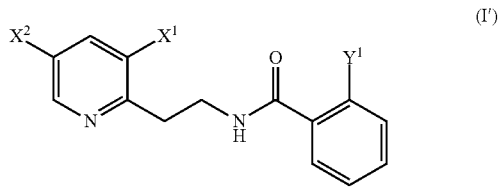

(I')

or a salt or N-oxide thereof, wherein
  $X^1$ and $X^2$ are independently selected from the group consisting of halogen, alkyl, and haloalkyl, provided that at least one of $X^1$ and $X^2$ is a haloalkyl; and Y[1] is selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

In one aspect, the compound is N-{2-[3-chloro-5-(trifluoromethyl)-2-pyridinyl]ethyl}-2-trifluoromethylbenzamide, which corresponds to formula (I'''):

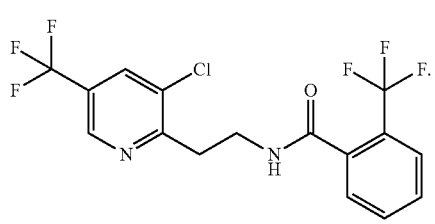

In one aspect, the applying is to a soybean seed, a soybean root, a soybean plant, or to soil in which soybean is growing or in which it is desired to grow, or a combination thereof. In one aspect, the applying is to a corn seed, a corn root, a corn plant, or to soil in which corn is growing or in which it is desired to grow, or a combination thereof. In one aspect, reducing the occurrence comprises reducing mean disease severity compared to seed, plants, or plant roots not treated with a compound of general formula (I). In one aspect, reducing the occurrence comprises reducing mean disease incidence compared to seed, plants, or plant roots not treated with a compound of general formula (I). In one aspect, reducing the occurrence comprises reducing mean defoliation compared to seed, plants, or plant roots not treated with a compound of general formula (I). In one aspect, reducing the occurrence comprises increasing yield as compared to seed, plants, or roots not treated with a compound of general formula (I).

In one embodiment, a method for reducing the occurrence of phytopathogenic fungi is provided, for example, wherein said fungi are selected from the group consisting of *Fusarium virguliforme* and *Fusarium tucumaniae*, comprising applying an effective amount of a composition comprising a compound of the general formula (I):

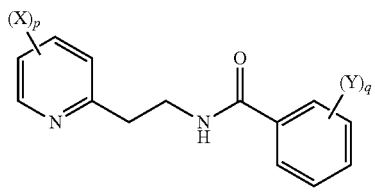

or a salt or N-oxide thereof to a plant seed, to soil in which a plant is growing or in which it is desired to grow it, to plant roots, or to combinations thereof;
wherein
p is an integer equal to 1, 2, 3 or 4;
q is an integer equal to 1, 2, 3, 4 or 5;
each X is independently selected from the group consisting of halogen, alkyl, and haloalkyl, provided that at least one X is a haloalkyl;

each Y is independently selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

In one aspect, p is 2. In one aspect, q is 1 or 2, and the substituent(s) Y is/are positioned in the ortho position of the benzene ring. In one aspect, the compound corresponds to the general formula (I'):

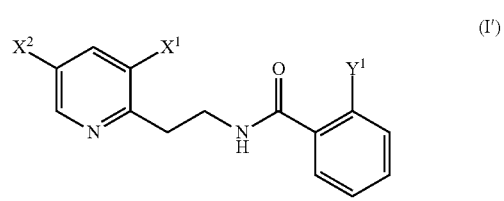

or a salt or N-oxide thereof, wherein
$X^1$ and $X^2$ are independently selected from the group consisting of halogen, alkyl, and haloalkyl, provided that at least one of $X^1$ and $X^2$ is a haloalkyl; and
Y[1] is selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

In one aspect, the compound is N-{2-[3-chloro-5-(trifluoromethyl)-2-pyridinyl]ethyl}-2-trifluoromethylbenzamide, which corresponds to formula (I'''):

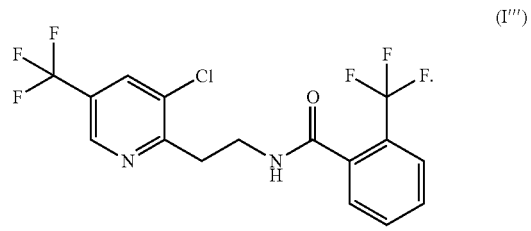 [SMILES: O=C(NCCc1ncc(C(F)(F)F)cc1Cl)c1ccccc1C(F)(F)F]

In one aspect, the applying is to a soybean seed, a soybean root, a soybean plant, or to soil in which soybean is growing or in which it is desired to grow, or a combination thereof. In one aspect, the applying is to a corn seed, a corn root, a corn plant, or to soil in which corn is growing or in which it is desired to grow, or a combination thereof. In one aspect, reducing the occurrence comprises reducing mean disease severity compared to seed, plants, or plant roots not treated with a compound of general formula (I). In one aspect, reducing the occurrence comprises reducing mean disease incidence compared to seed, plants, or plant roots not treated with a compound of general formula (I). In one aspect, reducing the occurrence comprises reducing mean defoliation compared to seed, plants, or plant roots not treated with a compound of general formula (I). In one aspect, reducing the occurrence comprises increasing yield as compared to seed, plants, or roots not treated with a compound of general formula (I).

In one embodiment, a soybean seed is provided, comprising an effective amount of a composition comprising a compound of the general formula (I):

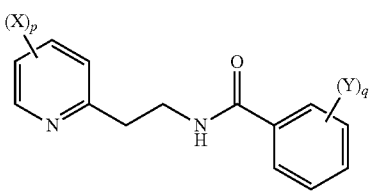

(I)

or a salt or N-oxide thereof, wherein
  p is an integer equal to 1, 2, 3 or 4;
  q is an integer equal to 1, 2, 3, 4 or 5;
  each X is independently selected from the group consisting of halogen, alkyl, and haloalkyl, provided that at least one X is a haloalkyl;
  each Y is independently selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

In one aspect, p is 2. In one aspect, q is 1 or 2, and the substituent(s) Y is/are positioned in the ortho position of the benzene ring. In one aspect, the compound corresponds to the general formula (I'):

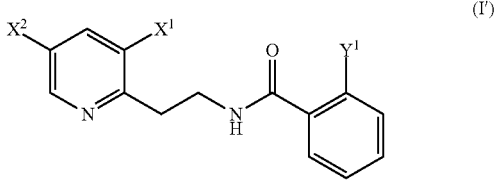

(I')

or a salt or N-oxide thereof, wherein
  $X^1$ and $X^2$ are independently selected from the group consisting of halogen, alkyl, and haloalkyl, provided that at least one of $X^1$ and $X^2$ is a haloalkyl; and
  $Y^1$ is selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

In one aspect, the compound is N-{2-[3-chloro-5-(trifluoromethyl)-2-pyridinyl]ethyl}-2-trifluoromethylbenzamide and corresponds to formula (I'''):

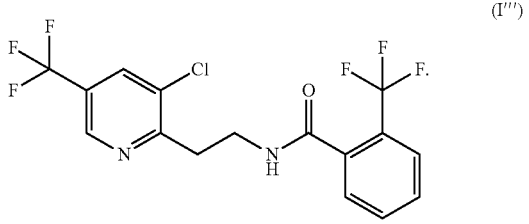 [SMILES: O=C(NCCc1ncc(C(F)(F)F)cc1Cl)c1ccccc1C(F)(F)F]

(I''')

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
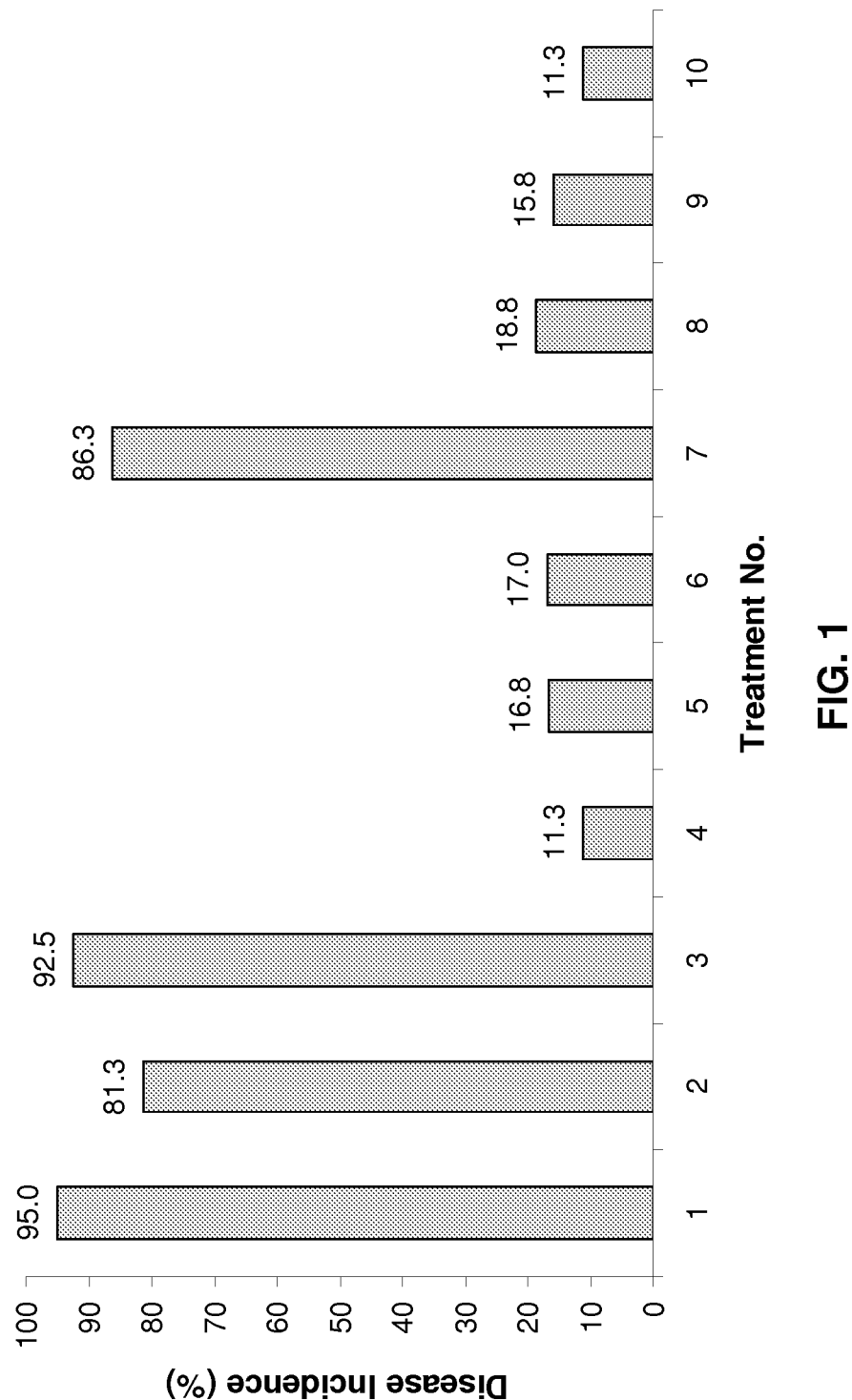
FIG. 1 shows disease incidence in soybean plants grown from seeds exposed to various treatment regimens.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

Other than in the operating examples, or where otherwise indicated, all numbers expressing quantities of ingredients, reaction conditions and so forth used in the specification and claims are to be understood as being modified in all instances by the term "about". Accordingly, unless indicated to the contrary, the numerical parameters set forth in the instant specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the instant disclosure are approximations, the numerical values set forth in the specific examples are reported as precisely as possible. Any numerical values, however, inherently contain certain errors necessarily resulting from the standard deviation found in their respective testing measurements.

It should also be understood that any numerical range recited herein is intended to include all sub-ranges subsumed therein. For example, a range of 1" to 10" is intended to include all sub-ranges between and including the recited minimum value of 1 and the recited maximum value of 10, that is, having a minimum value equal to or greater than 1 and a maximum value of equal to or less than 10.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

With respect to the present disclosure, the phrase "effective amount" as used herein is intended to refer to an amount of composition according to the instant disclosure which is sufficient to reduce the occurrence of sudden death syndrome. Such an amount can vary within a wide range depending on the fungus to be controlled, the type of plant, the climatic conditions, and the compounds included in the composition according to the instant disclosure.

As used herein, the term "plant" is intended to refer to any part of a plant (e.g., roots, foliage, shoot) as well as trees, shrubbery, flowers, and grasses. As used herein, the term "seed" is intended to include seeds, tubers, tuber pieces, bulbs, and the like, or parts thereof from which a plant is grown.

In the context of the present disclosure:

"Halogen" means chlorine, bromine, iodine or fluorine;

"Alkyl" means a straight or branched, and in general, saturated hydrocarbon radical having from one to the number of carbon atoms designated, for example $C_1$-$C_6$ alkyl, such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

"Acyl" means an organic radical derived from an organic acid by the removal of the hydroxyl group (e.g., RCO— is the acyl radical of RCOOH, whereby R is an alkyl, cycloalkyl, aryl, or aralkyl group which optionally may be substituted with one or more substituents such as amino, alkyl, cycloalkyl, alkoxy, or benzyl) such as, for example, acetyl, propionyl, benzoyl, or 1-amino-cyclohexanecarbonyl, and includes the term "alkanoyl," which is the organic radical RCO— in which R is an alkyl or cycloalkyl group as defined herein.

In one embodiment, each of the alkyl or acyl radicals present in the molecule contains from 1 to 10 carbon atoms, preferably from 1 to 7 carbon atoms, more preferably from 1 to 5 carbon atoms, and may be linear or branched;

"Haloalkyl" means an alkyl group in which some or all of the hydrogen atoms may be replaced by from one up to the maximum possible number of halogen atoms as mentioned above, for example $C_{1-6}$haloalkyl, chloroalkyl, bromoalkyl, dichloroalkyl, trichloroalkyl, fluoroalkyl, difluoroalkyl, trifluoroalkyl, chlorofluoroalkyl, dichlorofluoroalkyl, chlorodifluoroalkyl, $CF_3$, $CF_2CF_3$, $CHF_2$, $CHF_2$, and the like.

"Alkenyl" means an aliphatic hydrocarbon group containing a carbon-carbon double bond and which may be straight or branched. Branched means that one or more alkyl groups such as methyl, ethyl or propyl are attached to a linear alkenyl chain. The alkenyl group may be substituted by one or more halogen. Exemplary alkenyl groups include ethenyl, propenyl, n-butenyl, isobutenyl, 3-methylbut-2-enyl, n-pentenyl, heptenyl, octenyl and decenyl.

"Alkynyl" means an aliphatic hydrocarbon group containing a carbon-carbon triple bond and which may be straight or branched generally having about 2 to about 15 carbon atoms in the chain. Branched means that one or more alkyl groups such as methyl, ethyl or propyl are attached to a linear alkynyl chain. Exemplary alkynyl groups include ethynyl, propenyl, n-butynyl, 2-butynyl, 3-methylbutynyl, n-pentynyl, heptynyl, octynyl and decynyl.

Each of the alkenyl or alkynyl radicals present in the molecule generally contains from 2 to 10 carbon atoms, preferably from 2 to 7 carbon atoms, more preferably from 2 to 5 carbon atoms, and may be linear or branched.

"Alkoxy" means any unbranched or branched, substituted or unsubstituted, saturated or unsaturated alkyl-O— group in which the alkyl group is as previously described and the bond to the parent moiety is through the ether oxygen. Non-limiting examples of alkoxy groups include methoxy, ethoxy, n-propoxy, isopropoxy and n-butoxy. "Haloalkoxy" means any unbranched or branched, substituted or unsubstituted, saturated or unsaturated haloalkyl-O— group in which the haloalkyl group is as previously described and the bond to the parent moiety is through the ether oxygen. Non-limiting examples of haloalkoxy groups include $C_{1-6}$haloalkoxy, $C_{1-6}$-fluoroalkoxy, $OCF_3$, $OCHF_2$, $OCF_2CF_3$, and the like. "Halothioalkyl" means any unbranched or branched, substituted or unsubstituted, saturated or unsaturated thioalkyl group substituted with from one up to the maximum possible number of halogen atoms. Non-limiting examples of halothioalkyl groups include $C_{1-6}$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, and the like.

"Amino" means a group having the structural formula —$NH_2$; "aminoalkyl" an alkyl or substituted alkyl group as defined above bonded through one or more nitrogen (—NR—) atoms and includes, for example, the groups —NR—$C_{1-12}$alkyl, —NR—$C_{1-6}$alkylene, —NR—$C_{1-6}$ alkyl, etc. (where R is preferably hydrogen but may include alkyl or substituted alkyl as defined above); "dialkylamino" means a radical —NRR' where R and R' independently represent an alkyl, alkenyl, hydroxyalkyl, or haloalkyl group. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Alkylthio" means a radical —SR where R is an alkyl as defined above (e.g., $C_{1-6}$thio, methylthio, ethylthio, propylthio, butylthio, and the like).

"Hydroxyl" means a group having the structural formula —OH.

"Cyano" means a group having the structural formula —CN.

"Phenoxy" means a phenyl-O— group wherein the phenyl ring is optionally substituted with one or more ring system substituents such as alkyl, alkoxy, amino, hydroxyl, halogen, nitro, cyano, and combinations thereof (e.g., 4-propyl-2-methyl-, 2-chloro-4-methyl-, 3,4-diethoxy, 3-cyano-4-ethoxy-phenoxy and the like).

"Ester" means a group having the structural formula —RCOOR' and RCOOR'—.

"Benzyl" means a phenyl-$CH_2$— group. Substituted benzyl means a benzyl group in which the phenyl ring is substituted with one or more ring system substituents. Representative benzyls include 4-bromobenzyl, 4-methoxybenzyl, 2,4-dimethoxybenzyl, and the like.

"Sulfonyl" means a divalent radical, —$SO_2$—. "Halosulfonyl" means halo radicals attached to a sulfonyl radical. Examples of such halosulfonyl radicals include chlorosulfonyl and bromosulfonyl.

"Alkoxyalkenyl" means an alkenyl group substituted with one or more alkyl ether groups.

"Alkylsulfonamide" refers to the groups

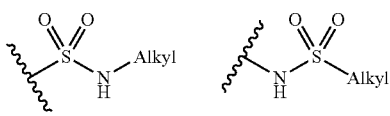

wherein alkyl has the same meaning as above.

"Nitro" means a group having the structural formula —NO$_2$.

"Alkylsulfonyl," "phenylsulfonyl," and "benzylsulfonyl" mean an alkyl-SO$_2$— group, a phenyl-SO$_2$— group, and a benzyl-SO$_2$— group, respectively, in which the alkyl group is as previously described. Preferred alkylsulfonyl groups are those in which the alkyl group is C$_{1-6}$ alkyl.

The composition according to the present disclosure may provide a synergistic effect. This synergistic effect allows a reduction of the chemical substances spread into the environment and a reduction of the cost of the fungal treatment. In the context of the present disclosure, the term "synergistic effect" is defined by the following formula (according to Colby SR. Calculation of the synergistic and antagonistic responses of herbicide combinations. *Weeds*. 1967; 15(1): 20-22, which is incorporated by reference in its entirety therefor):

$$E = x + y - \left(\frac{xy}{100}\right)$$

wherein E represents the expected percentage of inhibition of the disease for the combination of two compounds (I and II) at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect.

The presently disclosed composition useful for the methods of the present disclosure comprises at least one compound of the general formula (I):

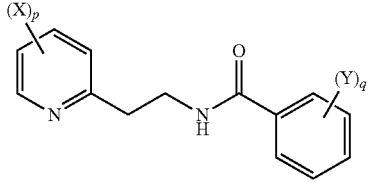

(I)

or a salt or N-oxide thereof, wherein:
  p is an integer equal to 1, 2, 3 or 4;
  q is an integer equal to 1, 2, 3, 4 or 5;
  each X is independently selected from the group consisting of halogen, alkyl, and haloalkyl, provided that at least one X is a haloalkyl;
  each Y is independently selected from the group consisting of halogen, alkyl, alkenyl, alkynyl, haloalkyl, alkoxy, amino, phenoxy, alkylthio, dialkylamino, acyl, cyano, ester, hydroxyl, aminoalkyl, benzyl, haloalkoxy, halosulfonyl, halothioalkyl, alkoxyalkenyl, alkylsulfonamide, nitro, alkylsulfonyl, phenylsulfonyl, and benzylsulfonyl.

The composition according to the present disclosure comprises a pyridinylethylbenzamide derivative of general formula (I). Preferably, the present disclosure relates to a composition comprising a pyridinylethylbenzamide derivative of general formula (I) wherein the different characteristics may be chosen alone or in combination as:
  p is 2;
  q is 1 or 2, and more preferably, q is 2;
  X is, independently of the others, halogen or haloalkyl, and more preferably X is, independently of the others, a chlorine atom or a trifluoromethyl group;
  Y is, independently of the others, halogen or haloalkyl, and more preferably Y is, independently of the others, a chlorine atom or a trifluoromethyl group;

In the context of the present disclosure, the substituents X of the 2-pyridine and the substituents Y of the benzene ring will be indexed in order to facilitate understanding. Thus, for example, if p is equal to 2 and q is equal to 1, the substituents termed "X" will be denoted by X$^1$ and X$^2$ and the substituent termed "Y" will be denoted by Y$^1$.

Preferentially, compounds of general formula (I) have the following characteristics, taken individually or in combination:
  p is chosen equal to 2, the substituents X$^1$ and X$^2$ being positioned as follows:

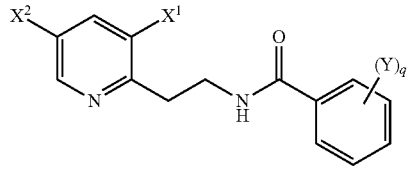

q is chosen equal to 1 or 2, the substituent(s) Y being positioned in the ortho position of the benzene ring.

A preferred subfamily of compounds according to the disclosure consists of the compounds corresponding to general formula (I'):

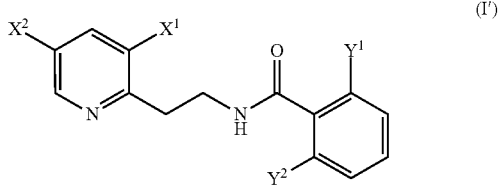

(I')

X and Y being as defined above. More preferably, X$^1$ is chosen as being halogen and X$^2$ is chosen as being haloalkyl.

Another preferred subfamily of compounds according to the disclosure consists of the compounds corresponding to general formula (I''):

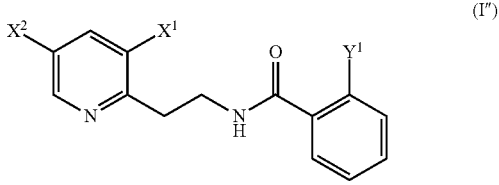

(I'')

the substituents X and Y being as defined above. More preferably, compound of general formula (I″) according to the present disclosure have the following characteristics, taken individually or in combination:

$X^1$ is chosen as being halogen and $X^2$ is chosen as being haloalkyl; and/or $Y^1$ is chosen as being halogen or haloalkyl.

Preferably, the haloalkyl group is chosen as being trifluoromethyl.

More preferably, the pyridinylethylbenzamide derivative of general formula (I) present in the composition of the present disclosure is:

N-{2-[3-chloro-S-(trifluoromethyl)-2-pyridinyl]ethyl}-2-trifluoromethylbenzamide;

N-{2-[3-chloro-S-(trifluoromethyl)-2-pyridinyl]ethyl}-2-iodobenzamide;

N-{2-[3,S-dichloro-2-pyridinyl]ethyl}-2-trifluoromethylbenzamide; or combinations thereof.

Even more preferably, the pyridinylethylbenzamide derivative of general formula (I) present in the composition of the present disclosure is N-{2-[3-chloro-S-(trifluoromethyl)-2-pyridinyl]ethyl}-2-trifluoromethylbenzamide, which corresponds to formula (I‴):

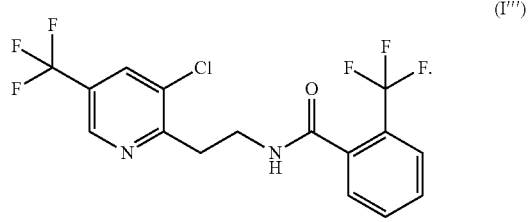

Compounds of general formula (I) and methods for their manufacture are disclosed in U.S. Pat. No. 7,572,818, for example, which is incorporated by reference in its entirety therefor.

Salts of general formula (I) include acid addition, alkali metal, and hydrochloride salts.

The present invention further comprises a seed at least partially coated with said composition.

The composition may be applied to at least a portion of a seed, prior to planting the seed. The composition may be applied in-furrow and/or as a root dip (as applicable) during planting of seeds or seedlings, and/or may be applied over the plant at or near emergence of the plant (e.g., via an irrigation system), and/or it may be applied during transplanting of established plants (e.g., plants having at least two mature leaves). The composition may be applied to seed in an amount of from about
$1\times10^{-4}$ to about 1000, from about $1\times10^{-3}$ to about 900, from about 0.01 to about 800, from about 0.1 to about 700, from about 1 to about 600, from about 5 to about 600, from about 10 to about 500, from about 25 to about 450, from about 50 to about 400, from about 75 to about 350, from about 100 to about 300, from about 150 to about 300, from about 200 to about 300, from about 225 to about 275, and from about 245 to about 255 grams (g) of active ingredient(s) per 100 kilograms (Kg) of seed. In particular embodiments of the present disclosure, the composition may be applied to seed in an amount of about 250 grams of active ingredient(s) per 100 Kg of seed. The composition may be applied in-furrow and/or as a root dip in an amount of from about 100 to about 2,500, from about 150 to about 2,250, from about 200 to about 2,000, from about 250 to about 1,750, from about 300 to about 1,500, from about 350 to about 1,250, from about 400 to about 1,000, from about 400 to about 750, from about 400 to about 700, from about 400 to about 650, from about 400 to about 600, from about 450 to about 550, and from about 475 to about 525 grams (g) of active ingredient(s) per hectare (ha). In particular embodiments of the present disclosure, the composition may be applied in-furrow and/or as a root dip in an amount of about 500 g of active ingredient(s) per ha (g/ha).

The presently disclosed method comprises applying a composition of the present disclosure to at least a part of a seed prior to planting of the seed, and/or application of the composition in-furrow and/or as a root dip (as applicable) during planting of a seed or seedling or during transplantation of a plant, wherein the composition comprises an effective amount of a fungicide such as, for example, compounds of general formula (I), and preferably fluopyram. The composition may be applied to at least a portion of the seed, prior to planting. The composition may be applied during planting (i.e., immediately prior to, concurrently with, or immediately following planting of the seed or seedling or transplant of the plant), and may be applied before or after row closure.

The presently disclosed method improves plant growth by reducing the incidence and/or symptoms of one or more fungal and/or nematicidal diseases including, for example, sudden death syndrome. Such fungal and/or nematicidal diseases include, inter alia, gray mold, powdery mildew, *Sclerotinia* diseases, *Monilia* diseases, pod and stem blight (*Phomopsis sojae* (*Diaporthe phaseolorum* var. *sojae*)), white mold (*Sclerotinia sclerotium*), charcoal rot (*Macrophomina phaseolina*), anthracnose (*Colletotrichum truncatum*), SCN infestation, and *Fusarium* diseases including sudden death syndrome (SDS).

Plants/Crops

Plants and seeds thereof that may be treated using the methods and compositions of the present disclosure include but are not limited to flowering and ornamental plants, shrubs, grasses, and crops. Crops (and seeds for said crops) which may be treated using the methods and compositions of the present disclosure include but are not limited to vines and table grapes, pome and stone fruit, vegetables and field crops, including strawberry, tomato, artichoke, *Brassicaceae*, bulb vegetables, canola, cereal grains, citrus, cotton, cucurbits, edible beans, fruiting vegetables, herbs and spices, hops, leafy vegetables, legume vegetables, peanut, berries, root and tuber vegetables, sunflower, tree nuts, maize, and soybean. Plants and seeds thereof most often treated by the methods and compositions of the present disclosure include those most vulnerable to or most often associated with the fungal and/or nematicidal diseases mentioned above, including but not limited to beans (e.g., adzuki, asparagus, broad (fava), bush, Chinese long, cluster, dry, edible-pod, field, garbanzo (chickpea), green, guar, Jack, kidney, lima, moth, mung, navy, red, rice, runner, snap, tepary, urd, yardlong, and wax beans), peas (e.g., blackeyed, cow (including catjang), crowder, dwarf, English, field, garden, green, pigeon, snow, Southern, and sugar snap peas), lentils, lupins (e.g., grain, sweet, sweet white, and white lupin), maize, and soybean in particular. The methods and compositions of the present disclosure are particularly suitable for reducing the incidence of sudden death syndrome (SDS) in soybean.

Genetically Modified Organisms

The composition may be applied to transgenic plants and plant cultivars which have been obtained by genetic engineering methods ("Genetically Modified Organisms"), if appropriate in combination with conventional methods, and parts and seeds thereof may also be treated. More preferably, plants and seeds of the plant cultivars which are in each case commercially available or in use are treated in accordance with the present disclosure.

Depending on the plant species or plant cultivars, their location, and growth conditions (e.g., soils, climate, vegetation period, diet), the treatment in accordance with the present disclosure may also result in superadditive ("synergistic") effects. For example, reduced application rates and/or a widening of the activity spectrum and/or an increase in the activity of the substances and compositions which can be used in accordance with the present disclosure, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible, which exceed the sum of the effects of the individual elements.

The transgenic plants or plant cultivars (i.e., those obtained by genetic engineering) which are preferred and to be treated in accordance with the present disclosure include all plants which, through the genetic modification, received genetic material which imparts particular advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, nematodes, phytopathogenic fungi, bacteria and/or viruses, and also increased tolerance of the plants to certain herbicidally active ingredients. Examples of transgenic plants which may be mentioned are the important crop plants, such as cereals (e.g., wheat, rice), maize, soybeans, potatoes, cotton, oilseed rape and also fruit plants (e.g., apples, pears, citrus fruits and grapes), and particular emphasis is given to maize, soybeans, potatoes, cotton and oilseed rape. Traits that are particularly emphasized are the increased defense of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), also referred to as "Bt plants". Traits that are furthermore particularly emphasized are the increased tolerance of the plants to certain herbicidally active ingredients, for example imidazolinones, sulfonylureas, ACCases, glyphosate or phosphinotricin (e.g., the "PAT" gene). The genes in question which impart the desired traits can also be present in combination with one another in the transgenic plants.

Examples of Bt plants which may be mentioned are maize varieties, cotton varieties, soybean varieties, and potato varieties which are sold under the trade names YIELD GARD® (e.g., maize, cotton, soya beans), KNOCKOUT® (e.g., maize), STARLINK® (e.g., maize), BOLLGARD® (cotton), NUCOTN® (cotton), and NEWLEAF® (potato). Examples of herbicide-tolerant plants which may be mentioned are maize varieties, cotton varieties and soya bean varieties which are sold under the trade names ROUNDUP READY® (tolerance to glyphosate, for example maize, cotton, soybean), LIBERTY LINK® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include the varieties sold under the name CLEARFIELD® (e.g., maize). These statements also apply to plant cultivars having these or still-to-be-developed genetic traits, which plant cultivars will be developed and/or marketed in the future.

Additional Ingredients

In certain embodiments of the present disclosure, the composition may further comprise one or more additional ingredients including but not limited to one or more safeners and/or pesticides, herbicides and/or additional fungicides, which—depending on the properties desired—may comprise between about 0.001% to about 99.9%, about 0.01% to about 99%, about 0.1% to about 98%, about 1% to about 97%, about 5% to about 80%, about 5% to about 75%, about 5% to about 70%, about 5% to about 65%, about 5% to about 60%, about 5% to about 55%, about 5% to about 50%, about 10% to about 40%, about 10% to about 35%, and about 10% to about 25% by weight of the composition. Pesticides include but are not limited to insecticides, bacteria, acaracides, nematacides and combinations thereof. In particular, additional ingredients may include one or more of antibiotic nematicides such as abamectin; carbamate nematicides such as benomyl, carbofuran, carbosulfan, and cleothocard; oxime carbamate nematicides such as alanycarb, aldicarb, aldoxycarb, and oxamyl; organophosphorous nematicides such as diamidafos, fenamiphos, fosthietan, phosphamidon, cadusafos, chlorpyrifos, diclofenthion, dimethoate, ethoprophos, fensulfothion, fostiazate, heterophos, isamidofos, isazofos, methomyl, phorate, phosphocarb, terbufos, thiodicarb, thionazin, triazophos, imicyafos, and mecarphon; biological nematicides such as *Myrothecium verrucaria, Burholderia cepacia, Bacillus chitonosporus, Bacillus firmus* (e.g., Strain I-1582), *Pasteuria usage,* and *Paecilomyces lilacinus* or nematicides of plant or animal origin such as harpin proteins, amino acid sequences or virus, viroid particles; bacteria exhibiting nematicidal, fungicidal and bactericidal properties, including but not limited to, *Bacillus argri, Bacillus aizawai, Bacillus albolactis, Bacillus amyloliquefaciens, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus* spp., *Bacillus subtilis, Bacillus thurngiensis, Bacillus unifagellatus,* plus those listed in the category of *Bacillus* Genus in Bergey's Manual of Systematic Bacteriology, First Ed. (1986) (hereby incorporated by reference in its entirety), *B. firmus* CNCM I-1582 spore, *B. cereus* strain CNCM I-1562 spore, *B. amyloliquefaciens* IN937a, *B. subtillis* strain GB03, and *B. pumulis* strain GB34; acephate, benalaxyl, benalaxyl-M, bupirimate, clozylacon, dimethirimol, ethirimol, furalaxyl, hymexazol, metalaxyl, metalaxyl-M, ofurace, oxadixyl and oxolinic acid, carbendazim, chlorfenazole, diethofencarb, ethaboxam, fuberidazole, pencycuron, thiabendazole, thiophanate, thiophanate-methyl and zoxamide, diflumetorim as inhibitor which acts on complex I of the respiratory chain; bixafen, boscalid, carboxin, fenfuram, flutolanil, fluopyram, furametpyr, furmecyclox, isopyrazam (9R component), isopyrazam (9S component), mepronil, oxycarboxin, penthiopyrad, thifluzamid as inhibitors which act on complex II of the respiratory chain; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as inhibitors which act on complex III of the respiratory chain, binapacryl, dinocap, fluazinam and meptyldinocap, fentin acetate, fentin chloride, fentin hydroxide and silthiofam, andoprim, blasticidin-S, cyprodinil, kasugamycin, kasugamycin hydrochloride hydrate, mepanipyrim and pyrimethanil, fenpiclonil, fludioxonil and quinoxyfen, biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin, aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole, benthiavalicarb, dimethomorph, flumorph, iprovalicarb, mandipropamid, polyoxins, polyoxorim, prothiocarb, validamycin A and valiphenal, carpropamid, diclocymet, fenoxanil, phthalide, pyroquilon and tricyclazole, acibenzolar-5-methyl, probenazole and tiadinil, Bordeaux mixture, captafol, captan, chlorothalonil, copper naphthenate, copper oxide, copper oxychloride, copper preparations such as, for example, copper hydroxide, copper sulfate, dichlofluanid, dithianon, dodine and its free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulfur and sulfur preparations such as, for example, calcium polysulfide, thiram, tolylfluanid, zineb and ziram, 2,3-dibutyl-6-chlorothieno[2,3-d]pyrimidin-4 (3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide (penflufen), N-{2-[1,1'-bi (cyclopropyl)-2-yl]phenyl}-3-(difluoromethyl)-1-methyl-1-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)-methyl] phenyl}-2-(methoxyimino)-N-methylethanamide, 2-chloro-N-(1,1,3-tri-methyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)-phenyl] ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl-]ethylidene}amino)-oxy]methyl}phenyl)ethanamide, (2E)-2-(methoxyimino)- N-methyl-2-{2-[(E)-({1-[3-(trifluoromethyl)phenyl] ethoxy}imino)methyl]phenyl}ethanamide, (2E)-2-{2-[({[(1E)-1-(3-{[(E)-1-fluoro-2-phenylethenyl]oxy}phenyl) ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy] phenyl}-N-ethyl-N-methylimidoformamide, O-{1-[4-methoxyphenoxy)methyl]-2,2-dimethylpropyl}1H-imidazole-1-carbothioate, N-[2-(4-{[3-(4-chlorophenyl) prop-2-yn-1-yl]oxy}-3-methoxyphenyl)ethyl]-N²-(methylsulfonyl)valinamide, 5-chloro-7-(4-methylpiperidin-1-yl)-6-(2,4,6-trifluorophenyl) [1,2,4] triazolo[1,5-a]pyrimidine, 5-amino-1,3,4-thiadiazole-2-thiole, propamocarb-fosetyl, 1-[(4-methoxyphenoxy) methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts thereof, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 8-hydroxyquinoline, 8-hydroxyquinoline sulfate, 5-methyl-6-octyl-3,7-dihydro[1,2,4]-triazolo[1,5-a]pyrimidine-7-amine, 5-ethyl-6-octyl-3,7-dihydro[1,2,4] triazolo[1,5-a]pyrimidine-7-amine, benthiazol, bethoxazin, capsimycin, carvone, chinomethionat, chloroneb, cufraneb, cyflufenamide, cymoxanil, cyprosulfamide, acetoprole, benclothiaz, chloropicrin, dazomet, DBCP, DCIP, 1,2-dichloropropane, 1,3-dichloropropene, furfural, iodomethane, metam, methyl bromide, xylenols, debacarb, dichlorophen, diclomezine, dicloran, difenzoquat, difenzoquat methylsulfate, diphenylamin, ecomat, ferimzone, flumetover, fluopicolide, fluoromide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl) imino]-methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)-methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N—{(Z)-[(cyclopropylmethoxy)imino][6-(difluoromethoxy)-2,3-difluorophenyl]methyl}-2-phenylacetamide, N-{(E)-[(cyclopropylmeth-oxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts thereof, phenazine-1-carboxylic acid, phenothrin, phosphoric acid and salts thereof, propamocarb fosetylate, propanosine-sodium, proquinazid, pyrrolnitrin, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'- phenyl-N'-prop-2-yn-1-ylthiophene-2-sulfonohydrazide, zarilamide, neonicotinoids such as 1-(6-chloro-3-pyridylmethyl)-N-nitroimidazolidin-2-ylideneamine (imidacloprid), 3-(6-chloro-3-pyridylmethyl)-1,3-thiazolidin-2-ylidenecyanamide (thiacloprid), $N^1$-[(6-chloro-3-pyridyl)methyl]-$N^2$-cyano-$N^1$-methylacetamidine (acetamiprid), 1-(2-chloro-1,3-thiazol-5-ylmethyl)-3-methyl-2-nitroguanidine (clothianidin), nitenpyram, 1-methyl-2-nitro-3-(tetrahydro-3-furylmethyl)guanidine (dinotefuran), and 3-(2-chloro-1,3-thiazol-5-ylmethyl)-5-methyl-1,3,5-oxadiazinan-4-ylidene (nitro)amine (thiamethoxam), and those fungicides identified in the Fungicide Resistance Action Committee ("FRAC") Code List ("FRAC Code List©—2010") and the FRAC List of Common Names©—2010 (which are hereby incorporated by reference in their entireties therefor) are suitable for use as additional ingredients in the composition of the present disclosure. Each of these is available commercially and may be used in the method of the present disclosure in amounts conventionally recommended for their intended use. In certain aspects, the one or more additional ingredients comprising the composition includes, but is not limited to, trifloxystrobin, imidacloprid, spirotetramat, *Bacillus firmus* (strain I-1582), and combinations thereof.

In general, the additional ingredients (if present) are from about $1 \times 10^{-4}$ to about 1000, from about $1 \times 10^{-3}$ to about 900, from about 0.01 to about 800, from about 0.01 to about 500, from about 0.01 to about 300, from about 0.01 to about 100, from about 0.01 to about 50, from about 0.01 to about 25, from about 0.01 to about 10, from about 0.01 to about 1, from about 0.05 to about 0.5, from about 0.07 to about 0.25, from about 0.08 to about 0.2, from about 0.09 to about 0.15 from about 0.1 to about 700, from about 0.1 to about 300, from about 1 to about 600, from about 1.6 to about 100, from about 5 to about 600, from about 5 to about 100, from about 5 to about 50, from about 5 to about 25, from about 5 to about 15, from about 5 to about 10, from about 7.5 to about 10, from about 10 to about 500, from about 25 to about 450, from about 50 to about 400, from about 50 to about 300, from about 50 to about 200, from about 50 to about 100, from about 50 to about 75, from about 55 to about 70, from about 60 to about 65, from about 75 to about 350, from about 100 to about 300, from about 150 to about 300, from about 200 to about 300, from about 225 to about 275, and from about 245 to about 255 grams (g) of active ingredient(s) per 100 kilograms (Kg) of seed.

In general, the additional ingredients (if present) are from about 1 to about 10,000, from about 1 to about 9,000, from about 1 to about 8,000, from about 1 to about 7,500, from about 1 to about 7,000, from about 1 to about 6,000, from about 1 to about 5,000, from about 1 to about 4,000, from about 1 to about 3,000, from about 1 to about 2,500, from about 1 to about 2,000, from about 1 to about 1,500, from about 1 to about 1,000, from about 1 to about 900, from about 1 to about 800, from about 1 to about 750, from about 1 to about 700, from about 1 to about 600, from about 1 to about 500, from about 1 to about 400, from about 1 to about 300, from about 1 to about 250, from about 2 to about 250, from about 3 to about 250, from about 4 to about 250, from about 5 to about 250, from about 5 to about 200, from about 5 to about 150, from about 5 to about 100, from about 5 to about 90, from about 5 to about 80, from about 5 to about 75, from about 5 to about 70, from about 5 to about 60, from about 5 to about 50, from about 5 to about 40, from about 5 to about 30, from about 5 to about 25, from about 5 to about 20, from about 5 to about 15, and from about 5 to about 10 µg/mL, which may be diluted to from about 100 to about 100,000, from about 100 to about 90,000, from about 100 to about 80,000, from about 100 to about 75,000, from about 100 to about 70,000, from about 100 to about 60,000, from about 100 to about 50,000, from about 100 to about 40,000, from about 100 to about 30,000, from about 100 to about 25,000, from about 100 to about 20,000, from about 100 to about 10,000, from about 100 to about 9,000, from about 100 to about 8,000, from about 100 to about 7,500, from about 100 to about 7,000, from about 100 to about 6,000, from about 100 to about 5,000, from about 100 to about 4,000, from about 100 to about 3,000, from about 100 to about 2,500, from about 100 to about 2,000, from about 100 to about 1,500, from about 100 to about 1,000, from about 125 to about 1,000, from about 150 to about 1,000, from about 175 to about 1,000, from about 200 to about 1,000, from about 225 to about 1,000, and from about 250 to about 1,000 mL/acre.

In general, the additional ingredients (if present) are from about 50 to about 10,000, from about 50 to about 9,000, from about 50 to about 8,000, from about 50 to about 7,500, from about 50 to about 7,000, from about 50 to about 6,000, from about 50 to about 5,000, from about 50 to about 4,000, from about 50 to about 3,000, from about 50 to about 2,500, from about 50 to about 2,000, from about 50 to about 1,500, from about 50 to about 1,000, from about 60 to about 1,000, from about 70 to about 1,000, from about 75 to about 1,000, from about 80 to about 1,000, from about 90 to about 1,000, from about 100 to about 1,000, from about 125 to about 1,000, from about 150 to about 1,000, from about 175 to about 1,000, from about 200 to about 1,000, from about 225 to about 1,000, and from about 250 to about 1,000 grams/acre.

Provided herein are improved compositions and methods for controlling microbial (e.g., bacterial, viral, or fungal) damage or infestations in plants and seeds. The unexpected effectiveness of the formulations disclosed represents a significant advance because the total amount of composition required to control microbial damage may be reduced without compromising crop yield. With some combinations of the invention, the degree of control over microbial damage or infestation is unexpectedly significantly greater than would be expected from the sum of the composition components alone (e.g., synergy is observed). Consequently, the amount of composition required to control said microbial damage or infestation in plants is significantly less than would be expected from the sum of the composition components alone. These findings dramatically improve the cost-benefit ratio while lowering the chances that microbial resistance will develop. Also, when treating seeds the space available to apply any composition is limited because seeds are relatively small. Thus, reducing the amount (volume) of composition required for control of microbial damage or infestation—without compromising efficacy—also represents a significant advance.

Seed

The composition is suitable especially for protection of seed of any plant variety which is used in agriculture, in greenhouses, in forests, or in gardening from the aforementioned diseases, from *Fusarium virguliforme*, from *Fusarium tucumaniae*, from soybean cyst nematode, and especially from SDS. More particularly, the seed can be that of cereals (such as wheat, barley, rye, millet and sorghum, and oats), maize, cotton, soybean, rice, potatoes, sunflower, beans, coffee, beet (e.g., sugar beet and fodder beet), peanut, vegetables (such as tomato, cucumber, onions and lettuce), lawns, and ornamental plants. Of particular significance is the treatment of the seed of cereals (such as wheat, barley, rye and oats), maize, rice, cotton, and especially soybean.

In the context of the present disclosure, the at least one compound of general formula (I) may be applied to the seed alone, or in a suitable formulation. Preferably, the seed to be treated is in a sufficiently stable state such that the treatment causes little to no damage. In general, treatment of the seed may take place at any point between harvesting and sowing. Typically, the seed used is separated from the plant and freed from cobs, shells, stalks, coats, hairs or the flesh of any fruit. For example, it is possible to use seed which has been harvested, cleaned, and dried to a moisture content of less than 15% by weight. Alternatively, it is also possible to use seed which, after drying, has been treated, for example, with water and then dried again. Preferably, the amount of the at least one general formula (I) compound and/or the amount of further additives applied to the seed is selected in an amount that germination of the seed is not affected adversely, and that the resulting plant is not damaged.

The composition can be applied directly to seeds (i.e., without comprising any further components and without having been diluted). In general, it is preferable to apply the composition to the seed in the form of a suitable formulation. Suitable formulations and methods for the treatment of seed are known to those of ordinary skill in the art and are described, for example, in the following documents, which are incorporated by reference therefor: U.S. Pat. No. 4,272,417; U.S. Pat. No. 4,245,432; U.S. Pat. No. 4,808,430; U.S. Pat. No. 5,876,739; US 2003/0176428 A1; WO 2002/080675 A1; and WO 2002/028186 A2.

For application to seeds, the composition in accordance with the present disclosure can be converted to customary seed dressing product formulations such as solutions, emulsions, suspensions, powders, foams, slurries and other coating compositions for seed, and ultra-low volume ("ULV") formulations. Such formulations are prepared in the known manner by mixing the active ingredient or active ingredient combinations with customary additives, for example customary extenders, solvents, diluents, dyes, wetters, dispersants, emulsifiers, antifoaming agents, preservatives, secondary thickeners, adhesives, gibberellins, and/or water. Dyes which may be present in the seed dressing product formulations usable in accordance with the present disclosure are all dyes which are customary for such purposes. Both pigments, which are sparingly soluble in water, and dyes, which are soluble in water, may be used. Examples of dyes include those known by the names Rhodamine B, C.I. Pigment Red 112 ("CI-12370"), and C.I. Solvent Red 1 ("Oil Pink"). Wetters which may be present in the seed dressing product formulations usable in accordance with the present disclosure are all substances which are conventionally used for the formulation of active agrochemical ingredients and for promoting wetting. Alkylnaphthalenesulfonates, such as diisopropyl- or diisobutylnaphthalenesulfonates, can be used with preference. Useful dispersants and/or emulsifiers which may be present in the seed dressing product formulations usable in accordance with the present disclosure are all nonionic, anionic and cationic dispersants which are conventionally used for the formulation of active agrochemical ingredients. Nonionic or anionic dispersants or mixtures of nonionic or anionic dispersants can be used with preference. Suitable nonionic dispersants include, in particular, ethylene oxide/propylene oxide block polymers, alkylphenol polyglycol ethers and tristryrylphenol polyglycol ethers, and their phosphated or sulfated derivatives. Suitable anionic dispersants are, in particular, lignosulfonates, polyacrylic acid salts and arylsulfonate/formaldehyde condensates. Antifoaming agents which may be present in the seed dressing product formulations usable in accordance with the present disclosure are all foam-suppressing substances conventionally used for the formulation of active agrochemical ingredients. Silicone antifoams and magnesium stearate can be used with preference. Preservatives which may be present in the seed dressing product formulations usable in accordance with the present disclosure are all substances which can be employed in agrochemical compositions for such purposes. Examples include dichlorophene and benzyl alcohol hemiformal. Secondary thickeners which may be present in the seed dressing product formulations usable in accordance with the present disclosure are all substances which can be employed in agrochemical compositions for such purposes. Cellulose derivatives, acrylic acid derivatives, xanthan, modified clays and finely divided silica are preferred. Adhesives which may be present in the seed dressing product formulations usable in accordance with the present disclosure are all customary binders which can be employed in seed dressing products. Preference is given to polyvinylpyrrolidone, polyvinyl acetate, polyvinyl alcohol and tylose. Gibberellins which may be present in the seed dressing product formulations usable in accordance with the present disclosure are preferably the gibberellins A1, A3 ("gibberellic acid", "GA", or "GA$_3$"), A4 and A7, particular preference being given to using gibberellic acid. The gibberellins are known (see, e.g., Chemie der Pflanzenschutz-und Schädlingsbekämpfungsmittel [Chemistry of Plant Protectants and Pesticides], Vol. 2, pp. 401-412 (R. Wegler ed., Springer Verlag 1970). When used as other than a seed coating (e.g., when used for application to soil or roots), the formulation may also contain the customary additives recited above. The additive content may comprise between about 0.1% and about 40%, about 5% and about 40%, about 10% and about 40%, about 20% and about 40%, about 30% and about 40%, about 0.1% and about 30%, about 0.1% and about 20%, about 0.1% and about 10%, and about 0.1% and about 5% by weight of the composition.

The seed dressing product formulations usable in accordance with the present disclosure can be employed either directly, or after prior dilution with water for the treatment of a wide range of seeds. For instance, the concentrates or the formulations obtainable by dilution with water can be used to dress the seed of cereals, such as wheat, barley, rye, oats and triticale, and the seed of maize, rice, rape, peas, beans, cotton, soybean, sunflowers, beet, and a wide variety of different vegetable seeds. The seed dressing product formulations usable in accordance with the present disclosure or the dilute preparations thereof can also be used to dress seed of transgenic plants. In this context, additional synergistic effects may also occur as a consequence of the interaction with the substances formed by expression of proteins by the transgenic plants.

Useful apparatus which can be used to treat seed with the seed dressing product formulations usable in accordance with the present disclosure, or with the preparations prepared therefrom by addition of water, is all mixing apparatus which can typically be used to dress seed. Specifically, the seed dressing procedure is to place the seed into a mixer, add the amount of seed dressing product formulation desired in each case, either as such or after prior dilution with water, and to then mix the contents of the mixer until the formulation has been distributed homogeneously on the seed. If appropriate, this is followed by a drying process.

The application rate of the seed dressing product formulations usable in accordance with the present disclosure can be varied within a relatively wide range. It is guided by the particular content of the active ingredients in the formulations and by the seed. The application rates of the active ingredient combinations are generally between about 0.001 to about 100, about 0.01 to about 75, about 0.1 to about 50, about 0.1 to about 25, about 0.1 to about 10, about 0.1 to about 5, about 0.1 to about 2.5, about 0.1 to about 1, about 0.1 to about 0.5, about 0.1 to about 0.4, about 0.1 to about 0.3, about 0.1 to about 0.25, and about 0.1 to about 0.2 grams of at least one general formula (I) compound per kilogram of seed.

Soil/Roots

In-furrow application is understood to mean the control of fungi and/or nematodes (including, but not limited to, *Fusarium virguliforme, Fusarium tucumaniae*, and/or soybean cyst nematode) by drenching the composition onto the soil, incorporating it into the soil, and in irrigation systems as droplet application onto the soil. The present disclosure relates to these application forms to natural (soil) or artificial substrates (e.g., rock wool, glass wool, quartz sand, pebbles, expanded clay, vermiculite), outdoors or in closed systems (e.g., greenhouses or under film cover) and in annual (e.g., vegetables, potatoes, cotton, beet, maize, soybean, or ornamental plants) or perennial crops (e.g., citrus plants, fruit, tropical crops, spices, nuts, vines, conifers and ornamental plants). It is also possible to deploy the active ingredients by the ultra-low volume (ULV) method or to inject the active ingredient formulation or the active ingredient itself into the soil. Root application is understood to mean the control of fungi and/or nematodes by applying the composition directly to plant roots (e.g., via immersion, dusting, or spraying).

For in-furrow and/or root application, the composition can be converted to the customary formulations such as solutions, emulsions, wettable powders, suspensions, powders, dusts, pastes, soluble powders, granules, suspension-emulsion concentrates, natural and synthetic materials impregnated with active ingredient, and microencapsulations in polymeric materials for in-furrow application. These formulations are produced in a known manner, for example by mixing the active ingredients with customary additives, such as extenders, that is, liquid solvents and/or solid carriers, optionally with the use of surfactants, that is, emulsifiers and/or dispersants, and/or foam formers. If the extender used is water, it is also possible, for example, to use organic solvents as cosolvents. The following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water. Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils. It is possible to use dyes such as inorganic pigments, for example iron oxide, titanium oxide and Prussian Blue, and organic colorants such as alizarin dyes, azo dyes and metal phthalocyanine dyes, and trace nutrients such as salts of iron, manganese, boron, copper, cobalt, molybdenum and zinc. The formulations generally contain between about 0.001 and about 99.9% by weight of active ingredient, and preferably between about 0.5 and about 90%. The additive content may comprise between about 0.1% and about 40%, about 5% and about 40%, about 10% and about 40%, about 20% and about 40%, about 30% and about 40%, about 0.1% and about 30%, about 0.1% and about 20%, about 0.1% and about 10%, and about 0.1% and about 5% by weight of the composition. The compositions may be present in commercially standard formulations and in the use forms, prepared from these compositions, as a mixture with other active ingredients, such as insecticides, attractants, sterilants, bactericides, acaricides, nematicides, fungicides, growth-regulating substances or herbicides, including those described above. For example, the insecticides may include phosphates, carbamates, carboxylates, chlorinated hydrocarbons, phenylureas and substances produced by microorganisms, inter alia. Mixing with other known active ingredients such as herbicides or with fertilizers and growth regulators is also possible. When used for other than in-furrow and/or root application (e.g., when used for application to seeds), the formulation may also contain the customary additives recited above. The active ingredient content of the use forms prepared from the composition may vary within wide limits, and may be from about $1 \times 10^{-7}$ to about 99.9% by weight of active ingredient, and preferably from about $1 \times 10^{-4}$ to about 50% by weight. The amount of the at least one compound of general formula (I) in the use forms prepared from the composition may also vary within wide limits, and may be from about $1 \times 10^{-7}$ to about 99.9% by weight of the at least one general formula (I) compound, and preferably from about $1 \times 10^{-5}$ to about 50% by weight.

A method for reducing the occurrence of SDS is also provided, comprising applying an effective amount of a composition as disclosed above to a seed, to soil in which a plant is growing or in which it is desired to grow it, to the roots of a plant, or combinations thereof. The applying may be performed as described above. In one embodiment, the composition comprises at least one compound selected from the group consisting of N-{2-[3-chloro-5-(trifluoromethyl)-2-pyridinyl]ethyl}-2-trifluoromethylbenzamide (commonly known as "fluopyram"); N-{2-[3-chloro-5-(trifluoromethyl)-2-pyridinyl]ethyl}-2-iodobenzamide; N-{2-[3-chloro-5-(trifluoromethyl)-2-pyridinyl]ethyl}-2-bromobenzamide, and combinations thereof. In one embodiment, the at least one compound is fluopyram. In one embodiment, the composition is applied to at least a portion of the seed. In one embodiment, the seed is substantially coated with the composition. In one embodiment, the composition is applied in-furrow during planting of a seed or seedling or during transplanting of established plants. In one embodiment, reducing the occurrence comprises reducing mean disease severity compared to seed or plants not treated with the instant composition and methods. In one aspect, reducing the occurrence comprises reducing mean disease incidence compared to seed, plants, or plant roots not treated with a compound of general formula (I). In one aspect, reducing the occurrence comprises reducing mean defoliation compared to seed, plants, or plant roots not treated with a compound of general formula (I). In one embodiment, reducing the occurrence comprises increasing yield (e.g., bushels/acre) of the plant as compared to seed or plants not treated with the instant composition and methods. In one embodiment, the seed, seedling, plant, or root is a soybean seed, seedling, plant, or root. In one embodiment, the seed, seedling, plant, or root is a maize seed, seedling, plant, or root.

Example 1

Soybean seeds (*Glycine max* (L.) Merr., an indeterminate line) were treated with Trilex® 2000 (7.12% (w/v) trifloxystrobin, 5.69% (w/v) metalaxyl), Gaucho® 600 FS (48.7% (w/v) imidacloprid), Votivo® 240 FS (21.5% (w/v) *Bacillus firmus* strain I-1582), and fluopyram (41.5% (w/v)) in the amounts and combinations shown in TABLE 1.

TABLE 1

| Treatment No. | Active Compound(s) | Amount(s) |
|---|---|---|
| 1 | — | — |
| 2 | Trilex ® 2000 | 8.66 ga/100 Kg |
|   | Gaucho ® 600 FS | 62.5 ga/100 Kg |
| 3 | Votivo ® 240 FS | 0.1 mga/seed |
| 4 | Fluopyram | 0.17 mga/seed |
| 5 | Fluopyram | 0.34 mga/seed |
| 6 | Fluopyram | 0.67 mga/seed |
| 7 | Trilex ® 2000 | 8.66 ga/100 Kg |
|   | Gaucho ® 600 FS | 62.5 ga/100 Kg |
|   | Votivo ® 240 FS | 0.1 mga/seed |
| 8 | Trilex ® 2000 | 8.66 ga/100 Kg |
|   | Gaucho ® 600 FS | 62.5 ga/100 Kg |
|   | Votivo ® 240 FS | 0.1 mga/seed |
|   | Fluopyram | 0.17 mga/seed |
| 9 | Trilex ® 2000 | 8.66 ga/100 Kg |
|   | Gaucho ® 600 FS | 62.5 ga/100 Kg |
|   | Votivo ® 240 FS | 0.1 mga/seed |
|   | Fluopyram | 0.34 mga/seed |
| 10 | Trilex ® 2000 | 8.66 ga/100 Kg |
|   | Gaucho ® 600 FS | 62.5 ga/100 Kg |
|   | Votivo ® 240 FS | 0.1 mga/seed |
|   | Fluopyram | 0.67 mga/seed |

FS = flowable concentrate for seed treatment
ga/100 Kg = grams of active compound per 100 kilograms of seed
mga/seed = milligrams of active compound per seed Seed growth and resistance to SDS were evaluated. Data on the incidence and severity of disease, plant vigor, plant count, plant density, defoliation, and yield were collected. Identification of SDS was based on the visual symptoms described in "Compendium of Soybean Diseases" (Glen Lee Hartman, J. B. Sinclair, and John Clark Rupe, eds. Am. Phytopathological Soc. 1999).

Disease incidence was defined as the percentage of plants in the plot with visible symptoms of SDS. For example, if all plants in a plot showed symptoms of SDS, the incidence value would be 100%. As shown in FIG. 1, soybean plants from seeds treated with fluopyram (with or without additional actives) showed significantly reduced disease incidence versus plants from seeds that did not receive fluopyram. Although Trilex 2000 (trifloxystrobin) and fluopyram are both fungicides, seeds treated with both trifloxystrobin and imidacloprid but not fluopyram (columns 2 & 7) showed less reduction of disease incidence than seeds treated with fluopyram alone (columns 4-6) or fluopyram in combination with other actives (columns 8-10). The values above each bar in FIG. 1 are the value of that bar along the y-axis.

Figure 2:
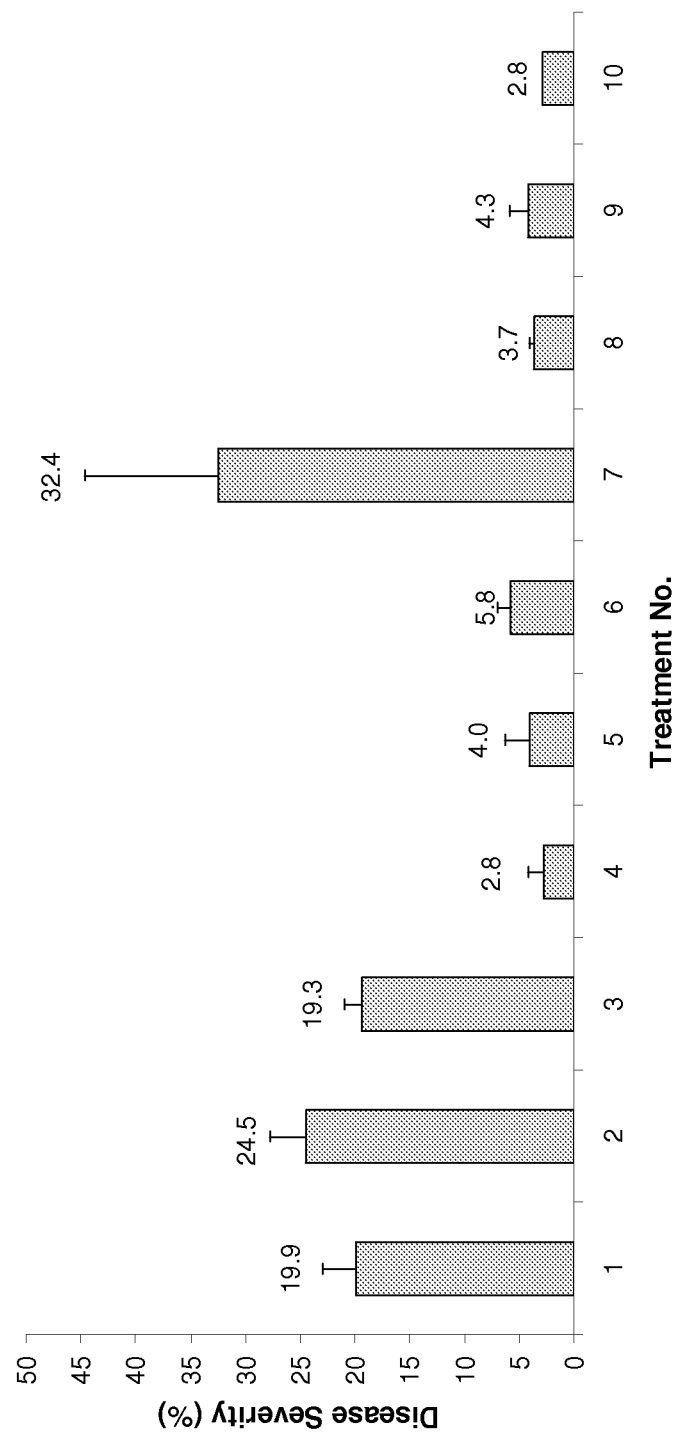
FIG. 2 shows disease severity in soybean plants grown from seeds exposed to various treatment regimens.

Symptoms of disease severity were determined as percent severity, on a scale of 0% to 100%, by examining the leaf area on the tops of plants and determining the area affected by SDS, expressed as a percentage of the total area. As shown by FIG. 2, soybean plants from seeds treated with fluopyram (columns 4-6 and 8-10) showed less disease severity than those from seeds that did not receive fluopyram (columns 1-3 and 7). Although trifloxystrobin (contained in Trilex® 2000) and fluopyram are both fungicides, seeds treated with both trifloxystrobin and the insecticide imidacloprid (Gaucho® 600 FS), as shown at column 2, demonstrated greater disease severity than seeds treated with fluopyram alone or fluopyram in combination with other actives. The error bars of FIG. 2 represent standard error, and the values above each bar are the value of that bar along the y-axis.

Vigor ratings, based on visual assessments of plant health, were collected according to the system shown in TABLE 2, with 1 being a healthy and vigorous plant and 6 being extremely low vigor.

TABLE 2

| Score | Standardized Vigor Rating Scale |
|---|---|
| 1 | Highly superior increase in vigor over market standard |
| 2 | Marked increase in vigor over market standard |
| 3 | Slight increase in vigor over market standard |
| 4 | Vigor equal to market standard |
| 5 | Vigor slightly inferior compared to market standard |
| 6 | Unacceptably inferior to market standard |

Figure 3:
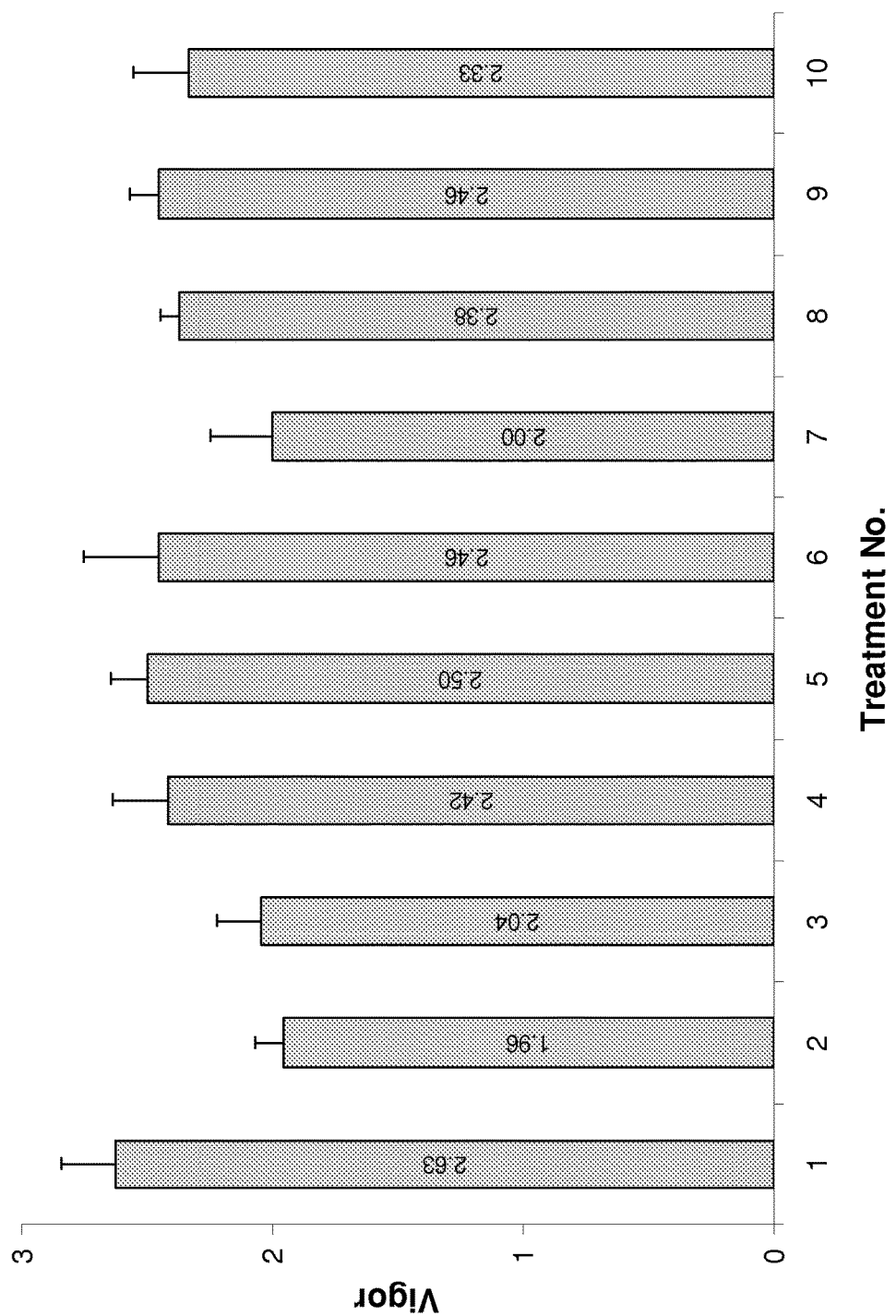
FIG. 3 shows the vigor of soybean plants grown from seeds exposed to various treatment regimens.

As shown in FIG. 3, all treatments showed improved vigor relative to untreated controls. The error bars of FIG. 3 represent standard error, and the values within each bar are the value of that bar along the y-axis. The vigor of plants from seeds treated with fluopyram (columns 4-6 and 8-10) was not adversely affected, and those plants demonstrated fewer SDS symptoms, as compared with plants from seeds that were not treated with fluopyram.

Figure 4:
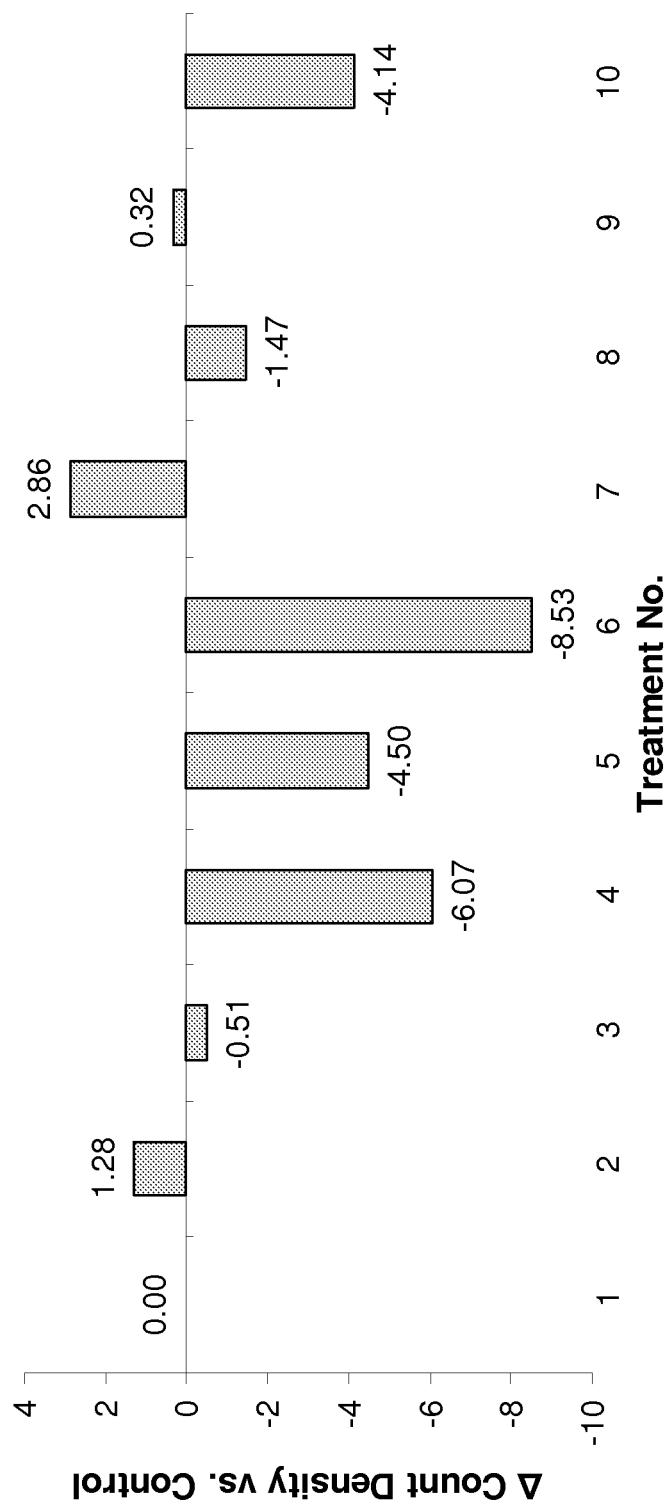
FIG. 4 shows the change in count density, versus control, of soybean plants grown from seeds exposed to various treatment regimens.

Plant density was calculated as the change in density versus controls. As shown in FIG. 4, treatment with fluopyram alone (columns 4-6) was associated with decreased count density versus control (column 1), as were treatments with 0.17 mg fluopyram/seed and 0.67 mg fluopyram/seed in combination with trifloxystrobin, metalaxyl, imidacloprid, and *Bacillus firmus* strain I-1582 (columns 8 & 10). The values above or below each bar are the value of that bar along the y-axis.

Figure 5:
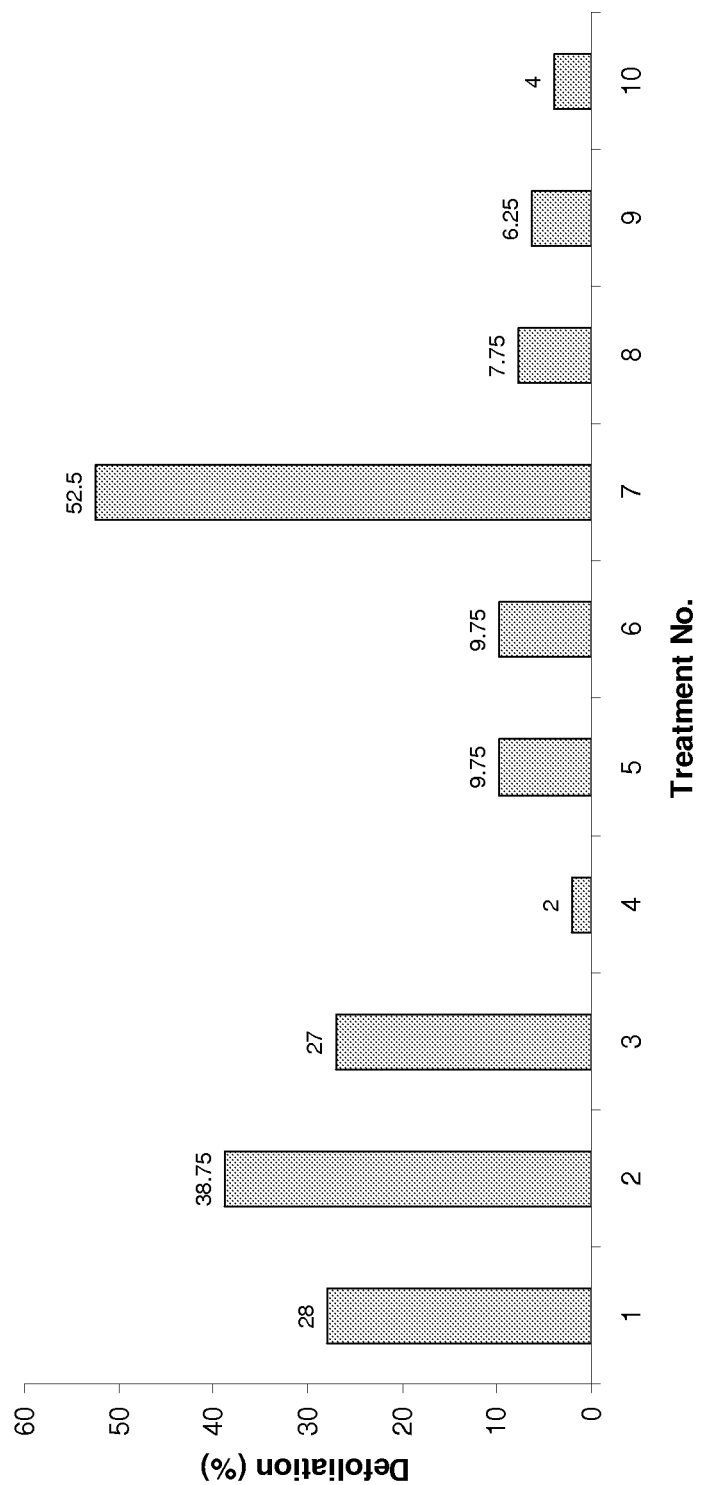
FIG. 5 shows the degree of defoliation in soybean plants grown from seeds exposed to various treatment regimens.

Defoliation was defined as the percentage of plants showing evidence of defoliation in a given plot (i.e., on a scale of 0% to 100%). As shown by FIG. 5, soybean plants from seeds treated with fluopyram (columns 4-6 and 8-10) showed less defoliation than those from seeds that did not receive fluopyram. Similar to the trend observed in FIG. 1, seeds treated with trifloxystrobin, metalaxyl, and imidacloprid, and/or with *B. firmus* strain I-1582 (columns 2, 3, and 7) showed greater defoliation than seeds treated with fluopyram alone or fluopyram in combination with other actives. The values above each bar are the value of that bar along the y-axis.

Figure 6:
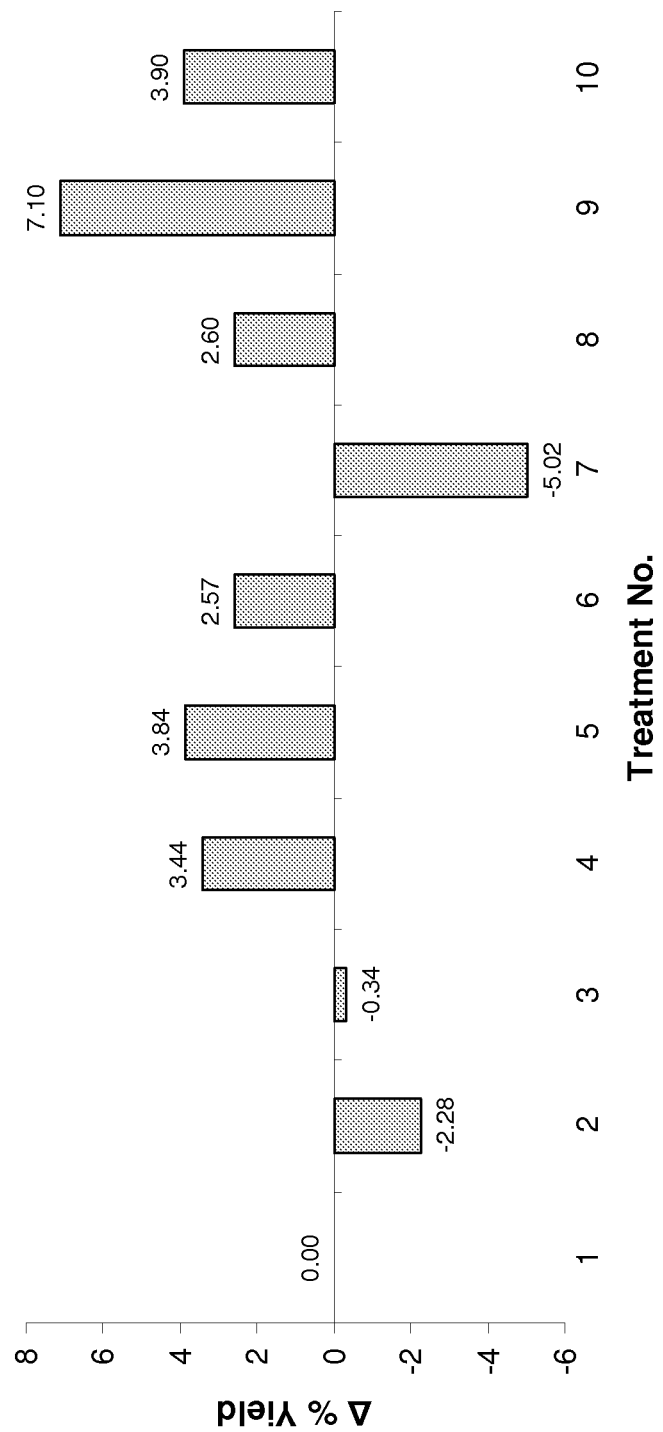
FIG. 6 shows percent yield, versus control, from soybean plants grown from seeds exposed to various treatment regimens.

To determine yield, soybeans were harvested from each plot, weighed, and their moisture content determined. The data from each treatment were normalized to the standard weight of 60 pounds of soybeans at 13% moisture. As shown by FIG. 6, soybean plants from seeds treated with fluopyram showed greater percent yield than those from seeds that were not treated with fluopyram. The values above or below each bar are the value of that bar along the y-axis.

Without wishing to be bound by theory, the applicant hypothesizes that the decreased incidence and severity of SDS observed in plants from seed treated with fluopyram contributes to improved vigor and reduced defoliation, which in turn contributes to improved yield. This result is surprising because the efficacy of fluopyram against *Fusarium* is low, relative to other fungi.

TABLE 3

| Fungus | Fluopyram Efficacy |
|---|---|
| Botrytis | ++++ |
| Powdery mildews | ++++ |
| Sclerotinia | ++++ |
| Monilinia | ++++ |
| Mycosphaerella | ++++ |
| Sigatoka | ++++ |
| Venturia | +++ |
| Alternaria | +++ |
| Pyrenophora | +++ |
| Didymella | ++ |
| Cylindrocladium | ++ |
| Septoria | ++ |
| Colletotrichum | ++ |
| Anthracnose | + |
| Fusarium | + |
| Rusts | + |

++++ = Excellent
+++ = Good
++ = Acceptable
+ = Low

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method for reducing the occurrence of sudden death syndrome in soybean, comprising
    applying an effective amount of
    N-{2-[3-chloro-5-(trifluoromethyl)-2-pyridinyl]ethyl}-2-trifluoromethylbenzamide of formula (I'''):

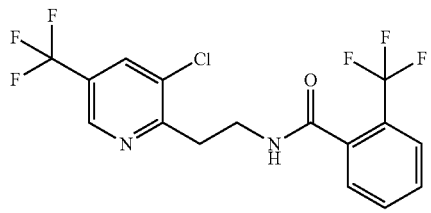

(I''')

or a salt or N-oxide thereof;
metalaxyl;
*Bacillus firmus* strain I-1582;
trifloxystrobin; and
imidacloprid;
to a soybean seed, soybean plant, to soil in which a soybean-plant is growing or in which it is desired to grow it, to soybean roots, or to combinations thereof; to thereby reduce the occurrence of sudden death syndrome in the soybean.

2. The method of claim 1, wherein the applying is to a soybean seed, a soybean root, or to soil in which soybean is growing, or to a combination thereof.

3. The method of claim 1, wherein reducing the occurrence comprises reducing mean disease severity compared to soybean seed, soybean plants, or soybean plant roots not treated with a compound of formula (I'''), metalaxyl, *Bacillus firmus* strain I-1582, trifloxystrobin, and imidacloprid.

4. The method of claim 1, wherein reducing the occurrence comprises increasing yield as compared to soybean seed, soybean plants, or soybean roots not treated with a compound of formula (I'''), metalaxyl, *Bacillus firmus* strain I-1582, trifloxystrobin, and imidacloprid.

5. The method of claim 1, wherein reducing the occurrence comprises reducing mean defoliating compared to soybean seed, soybean plants, or soybean plant roots not treated with the compound (I'''), metalaxyl, *Bacillus firmus* strain I-1582, trifloxystrobin, and imidacloprid.

6. The method of claim 1, wherein reducing the occurrence comprises reducing mean disease incidence compared to soybean seed, soybean plants, or soybean plant roots not treated with the compound (I'''), metalaxyl, *Bacillus firmus* strain I-1582, trifloxystrobin, and imidacloprid.

7. A method for reducing the occurrence of phytopathogenic fungi in soybean, wherein said fungi are selected from the group consisting of *Fusarium virguliforme* and *Fusarium tucumaniae*, comprising applying an effective amount of N-{2-[3-chloro-5-(trifluoromethyl)-2-pyridinyl]ethyl}-2-trifluoromethylbenzamide of formula (I'''):

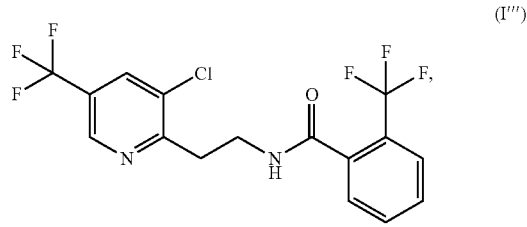 [SMILES: O=C(NCCc1ncc(C(F)(F)F)cc1Cl)c1ccccc1C(F)(F)F]

(I''')

or salt or N-oxide thereof;
metalaxyl;
*Bacillus firmus* strain I-1582;
trifloxystrobin; and
imidacloprid;
to a soybean seed, soybean plant, to soil in which a soybean plant is growing or in which it is desired to grow it, to soybean plant roots, or to combinations thereof.

8. The method of claim 7, wherein the applying is to a soybean seed, a soybean root, or to soil in which soybean is growing or to a combination thereof.

9. The method of claim 7, wherein reducing the occurrence comprises reducing mean disease severity compared to soybean seed, soybean plants, or soybean plant roots not treated with a compound of formula (I'''), metalaxyl, *Bacillus firmus* strain I-1582, trifloxystrobin, and imidacloprid.

* * * * *